US008615971B2

(12) United States Patent
Freudelsperger (10) Patent No.: US 8,615,971 B2
(45) Date of Patent: Dec. 31, 2013

(54) AUTOMATIC TABLET FILLING METHOD AND SYSTEM

(75) Inventor: Karl Freudelsperger, Hart bei Graz (AT)

(73) Assignee: Knapp Logistik Automation GmbH, Hart Bei Graz (AT)

(*) Notice: Subject to any disclaimer, the term of this patent is extended or adjusted under 35 U.S.C. 154(b) by 575 days.

(21) Appl. No.: 10/598,734

(22) PCT Filed: Mar. 3, 2005

(86) PCT No.: PCT/AT2005/000067
§ 371 (c)(1),
(2), (4) Date: Feb. 5, 2007

(87) PCT Pub. No.: WO2005/087175
PCT Pub. Date: Sep. 22, 2005

(65) Prior Publication Data
US 2007/0162179 A1 Jul. 12, 2007

(30) Foreign Application Priority Data
Mar. 11, 2004 (AT) .................................. A 429/2004

(51) Int. Cl.
*B65B 1/04* (2006.01)
(52) U.S. Cl.
USPC .................................. 53/473; 53/474; 53/154
(58) Field of Classification Search
USPC .................................. 53/473, 474, 411, 154
See application file for complete search history.

(56) References Cited

U.S. PATENT DOCUMENTS 4,736,849 A * 4/1988 Leonard et al. ............... 206/534
5,208,762 A * 5/1993 Charhut et al. ............... 700/216
(Continued)

FOREIGN PATENT DOCUMENTS

EP 1 528 500 A1 * 5/2005 .............. G06F 19/00

*Primary Examiner* — Hemant M Desai
*Assistant Examiner* — Gloria R Weeks
(74) *Attorney, Agent, or Firm* — Workman Nydegger (57) ABSTRACT

A system for automatically filling tablets into tablet containers comprising at least one tablet compartment for receiving tablets comprises:
reception means (30) for receiving a patient order containing a patient identification (PAT-ID) and at least one prescription comprising prescription data (REZ) regarding the types of tablets to be taken by the patient and instructions for taking said tablets;
allocation means (40) for allocating the prescription data (REZ) and patient identification (PAT-ID) to respective tablet containers (1);
at least one automatic tablet dispenser (50) containing supplies of a plurality of tablet types for automatically filling at least one tablet compartment of a respective tablet container, wherein the allocation means (40) or the automatic tablet dispenser (50) is/are designed for determining, from the prescription data (REZ), the number of tablets of the respective types of tablets to be taken by a patient at certain times and for allocating a tablet compartment (2) of a tablet container (1) to each determined time for taking the tablets, and the automatic tablet dispenser (50) is designed for filling the tablets thus determined for each determined time for taking them into the tablet compartment (2) of the respective tablet container (1), which compartment has been allocated.

26 Claims, 3 Drawing Sheets

(56) References Cited

U.S. PATENT DOCUMENTS

| | | | |
|---|---|---|---|
| 5,348,061 A | 9/1994 | Riley et al. | |
| 5,788,974 A * | 8/1998 | D'Amico et al. | 424/405 |
| 5,950,630 A * | 9/1999 | Portwood et al. | 128/897 |
| 6,006,946 A * | 12/1999 | Williams et al. | 221/9 |
| D421,899 S * | 3/2000 | Eneroth et al. | D9/732 |
| 6,152,364 A * | 11/2000 | Schoonen et al. | 235/375 |
| 6,187,291 B1 * | 2/2001 | Weinstein et al. | 424/45 |
| 6,256,967 B1 * | 7/2001 | Hebron et al. | 53/501 |
| 6,318,051 B1 | 11/2001 | Preiss | |
| 6,375,956 B1 * | 4/2002 | Hermelin et al. | 424/400 |
| RE37,829 E | 9/2002 | Charhut et al. | |
| 6,449,921 B1 | 9/2002 | Kim | |
| 6,471,089 B2 * | 10/2002 | Liff et al. | 221/13 |
| 6,580,968 B1 * | 6/2003 | Yuyama et al. | 700/241 |
| 6,735,497 B2 * | 5/2004 | Wallace et al. | 700/231 |
| 6,898,919 B2 * | 5/2005 | Kim | 53/154 |
| 6,951,353 B2 * | 10/2005 | Kozlowski et al. | 283/81 |
| 6,988,619 B2 * | 1/2006 | Klatt | 206/534 |
| 7,010,899 B2 * | 3/2006 | McErlean et al. | 53/135.2 |
| 7,334,379 B1 * | 2/2008 | Siegel et al. | 53/55 |
| 2007/0125046 A1 * | 6/2007 | Siegel et al. | 53/471 |

* cited by examiner

AUTOMATIC TABLET FILLING METHOD AND SYSTEM

The invention relates to a method and a system for automatically filling tablets into tablet containers comprising at least one tablet compartment for receiving tablets.

From the republished U.S. Pat. No. RE37,829, a system and a method for the automated filling of tablet containers with tablets according to a written prescription is known. This known tablet filling system comprises the following processing means:

a) means for receiving a patient order containing at least one prescription and patient information;

b) allocation means for allocating the prescriptions to automatic tablet filling lines, which, in turn, comprise:

c) tablet filling means for filling tablets into sealable tablet containers as per the prescription, wherein the tablets can be selected from a plurality of different types of tablets and each type of tablet is filled into a separate tablet container d) labelling means for labelling the tablet containers, the labels containing the name of the tablet type and optionally instructions for taking the tablet;

e) means for placing the cap in order to seal the tablet containers;

f) tablet-container sorting means for automatically sorting the filled tablet containers according to the patient order, and g) collecting means for automatically combining tablet containers belonging to a respective patient order;

g) transporting means for conveying the tablet containers to the individual processing means.

This system for filling tablet containers with tablets according to a written prescription has proven to be of value in large pharmacies where the individual types of tablets are not stored in small amounts after having been pre-packed in individual boxes, but are stored loose in large containers from which the required number of pieces is then counted and delivered as per the prescription.

Although the object of partitioning the types of tablets into individual tablet containers has been achieved satisfactorily by means of the known system, it has been shown that taking medicaments from individual tablet containers poses an absolutely serious problem especially for elderly people or people suffering from chronic diseases, since usually those people must themselves compose the correct formulation from a plurality of medicaments at the right time of day, which is asking too much of many patients due to senescent forgetfulness or other physical and mental impairments associated with their disease pattern. For patients in nursing homes, said supply with medicaments can be ensured by the nursing staff. However, patients under home care are on their own in this respect. Studies indicate that approx. 75% of prescribed medicaments are not taken according to instructions and thus confirm the above illustrated problem. Likewise, the prescribed medicaments are not always used up completely before new packages of medicaments are obtained. Thus, for medical and economic reasons, there is an urgent need for solving this problem.

Pharmacists have already identified this problem of many patients' inability to take the medicaments prescribed to them at the correct time and in the correct dosage. Therefore, as a customer service, pharmacists offer those patients to fill weekly rations of medicaments into blister packs, which can be collected by the patient from the pharmacy. Such blister packs are usually divided into seven weekdays. For each weekday, further partitions (morning, noontime, evening and night) are provided. Those blister packs are filled manually with the medicaments predetermined for the patient. Subsequently, the blister is sealed and provided with patient-specific data. However, this manual filling is very time-consuming and thus expensive and places a great burden on the people concerned with it, since the activity is, on the one hand, utterly monotonous while at the same time being, on the other hand, extremely responsible, as incorrect fillings could cause severe damage to the patient's health. Furthermore, it is difficult to maintain certain safety and control standards regarding medical law when filling is done manually.

For those reasons, there is still a need for an automated system for filling tablet containers with various types of tablets in a predetermined number of pieces, by means of which system the producer of pharmaceutical products or the wholesaler of pharmaceutical products is already able to fill said tablet containers. Pharmacies which deliver the completely filled tablet containers to the patients are thereby intended for providing a distribution network.

The present invention solves the above-described problems by providing a method for automatically filling tablets into tablet containers having the features of claim 1, as well as by providing a system for automatically filling tablets into tablet containers having the features of claim 11. Advantageous embodiments of the invention are set forth in the dependent claims.

By means of the present invention, it is possible to automatically fill tablet containers comprising one or preferably several compartments in such a way that precisely the medication which the patient is required to take at a certain time will be contained in a tablet compartment. Advantageously, the tablet containers are provided with seven tablet compartments (one for each day of the week) or with a multiple of seven compartments if medicaments have to be taken several times a day. The tablet containers are advantageously designed as blisters.

It should be mentioned that the term "tablet" as used herein comprises any solid medicament to be administered orally, i.e., also capsules and pills.

In a preferred embodiment of the invention, the allocation of prescription data and patient identification to respective tablet containers comprises the transmission of prescription data and patient identification to one or several information carriers and the allocation of a respective information carrier to one tablet container at a time. Due to such measures, there is a firm association between patient and prescription data and the tablet container at any point of time in the tablet filling process. The filling process can thus proceed in a controlled, largely decentralized manner; verifications of the progress of the process as well as of the faultless execution thereof are feasible at every processing station in the tablet filling system. For this purpose, the tablet containers and the information carriers allocated thereto are conveyed jointly through the at least one automatic tablet dispenser, which reads out prescription data stored on the information carrier, determines the number of tablets of the respective types of tablets to be taken by the patient at certain times and allocates a tablet compartment to each determined time for taking the tablets and fills the number of tablets required in each case into the respective tablet compartment that has been allocated. Thus, the data traffic toward a higher-ranking host control system is substantially reduced. Electronic data carriers, which preferably are writable and readable in a contactless manner, or printable substrates such as bar-code labels are provided as information carriers.

For the benefit of the patient, a plausibility check of the prescription data regarding a possible overdosage and the mutual compatibility between tablet types is suitably carried out already upon receiving the patient order and, in case an overdosage or an incompatibility is detected, the patient order is rejected.

Furthermore, the proper taking of the prescribed tablets is substantially facilitated for the patient if the tablet containers are automatically provided with information derived from the prescription data, such as instructions for taking the tablets. For the delivery of the filled tablet container to a patient, the tablet container is suitably provided with information derived from the patient identification, such as name and address, preferably by imprinting or labelling the tablet container.

So as to avoid any risk for the patient, in one embodiment of the invention it is provided that, if errors occur during the implementation of the tablet filling process for a tablet container, the tablet filling process is stopped and the tablet container is eliminated. Thereby, it is suitable that error identifications are writted onto the information carriers of the tablet containers which are being processed and tablet containers marked with error identifications are eliminated centrally at the end of the filling process, if problems or errors arise during the execution of the tablet filling process. In order to avoid that tablet containers already marked as defective are continued to be filled with tablets, it is suitable that, prior to each processing step of the tablet filling process, it is checked for each tablet container as to whether the information carrier allocated to said tablet container contains an error identification and, upon detection of such an error identification, the respective processing step is not carried out.

In order to simplify the delivery of tablet containers to a patient, it is advantageous if all tablet containers belonging to a respective patient order are collected automatically.

Since the tablet containers which presently are commonly used consist of a deep-drawn plastic film and have little mechanical load-bearing capacity, it is provided in an advanced embodiment of the invention that for each tablet container a support facility is provided on which the tablet container is conveyable through the tablet filling system. Damage to the tablet container is thereby avoided and the processing speed of the tablet filling system can be accelerated substantially. The support facility remains in the tablet filling system so that the manufacturing costs associated therewith—compared to the manufacturing costs for disposable tablet containers—can be taken into account less, since they can be used for a long period of time and their number is relatively low. Therefore, it is also suitable to place the information carrier on the support facility, thus being able to use the former multiple times.

For increasing operational reliability, it has turned out to be suitable to assemble the automatic tablet dispensers in a modular fashion from a plurality of tablet dispensing stations, each containing a supply of a tablet type and dispensing an adjustable number of tablets to random tablet compartments of the tablet containers.

In an easily maintainable and refillable embodiment of the tablet filling system according to the invention, each tablet dispensing station comprises a plurality of tablet dispensing units supplied by a common tablet magazine, with the tablet dispensing units preferably being designed as rotary dispensing units. Furthermore, the tablet magazine can be connectable to a replaceable buffer container, whereby various precautions can be taken in order to avoid confusions, such as, for example, hardware-related codings.

The invention is now illustrated in further detail by way of a non-limiting exemplary embodiment, with reference to the drawings. In the drawings.

Figure 1:
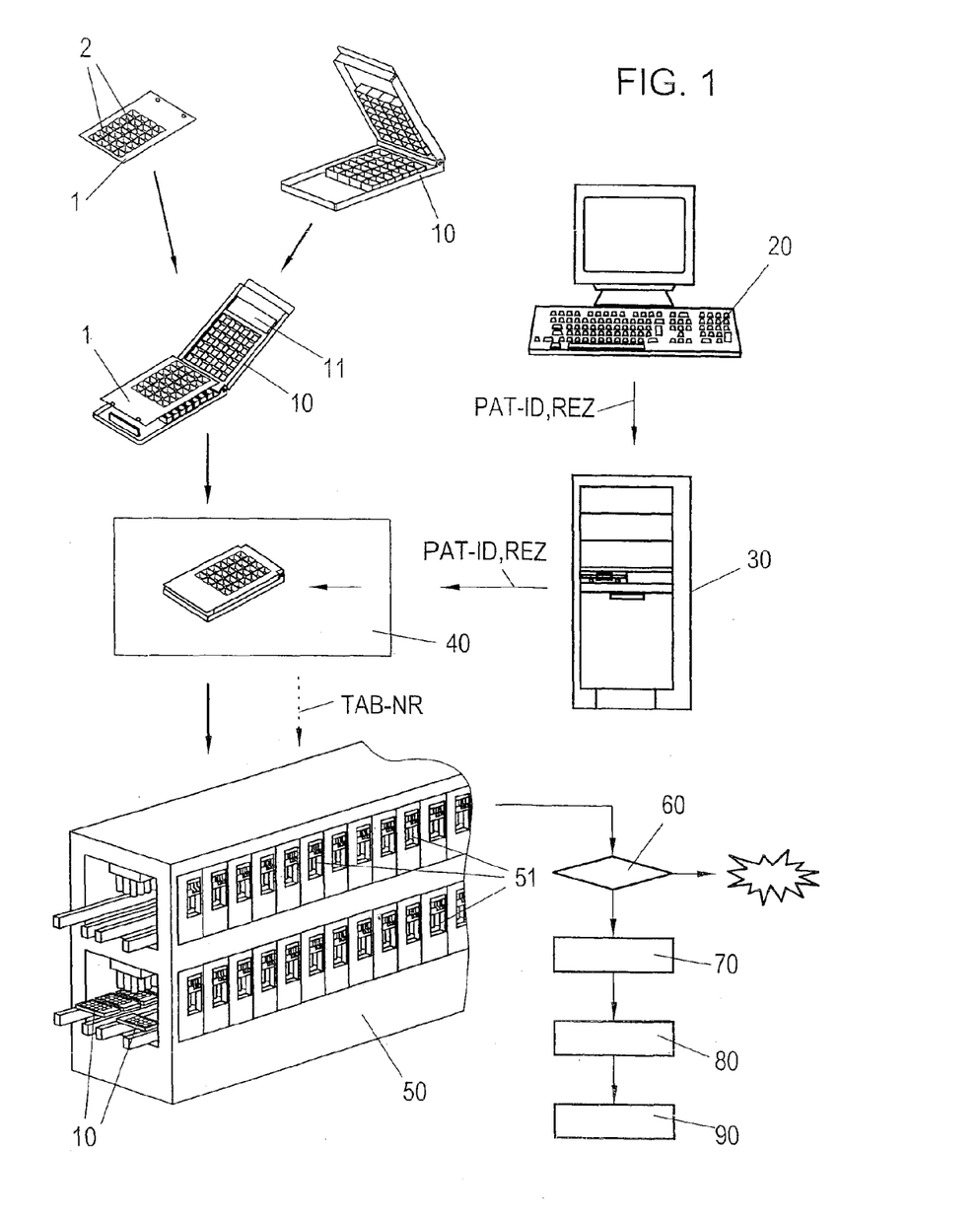
FIG. 1 shows a schematic illustration of the tablet filling system according to the invention.

The tablet filling system according to the invention as illustrated in FIG. 1 serves for automatically filling medicaments prescribed by a physician to a patient in the intended single dose into the tablet compartments of a tablet container. For this purpose, the prescription data REZ along with patient identification data PAT-ID such as a patient's name and address are either transmitted directly by a physician in electronic form via a computer 20 to reception means 30 of the tablet filling system according to the invention, or the physician's written prescription is handed over by the patient to a pharmacist who converts the prescription into an electronic format and sends the prescription data REZ along with the patient identification data PAT-ID via a computer to the reception means 30 of the tablet filling system. The transmission of those patient orders to the reception means 30 is performed continuously. Subsequently, the patient order is added by the reception means 30 to a FIFO ("first in, first out") chain in order to be processed in the sequence that has occurred, i.e., in order to commission the prescribed tablets in the production store into tablet containers, subsequently seal the tablet container, provide the same with customized data and make it available for further use in a dispatch area. It should be mentioned that prescriptions having the status "urgent" can be handled separately. In order to carry out this processing, the reception means 30 forward the patient order, i.e., the patient identification PAT-ID and at least one prescription comprising prescription data REZ regarding the types of tablets to be taken by the patient and instructions for taking said tablets, to allocation means 40, where the prescription REZ and the patient identification PAT-ID are allocated to respective tablet containers 1 comprising a plurality of tablet compartments 2. In a variant of said embodiment, the allocation means first determine from the prescription data REZ the number TAB-NR of tablets of the respective types of tablets to be taken by a patient at certain times and allocate this information to respective tablet compartments of a tablet container or, respectively, forward said information to a subsequent automatic tablet dispenser 50. However, in the basic version of the tablet filling system according to the invention, the automatic tablet dispenser 50 is designed for determining, by itself, the required number of tablets and the tablet compartments 2 in which the tablets are to be positioned from the prescription data REZ allocated to the tablet container 1 to be filled.

In order to keep the tablet filling system according to the invention independent of tablet containers which are to be used or, respectively, in order to take into account the poor transport properties of common tablet containers, a support facility 10 is used as illustrated in FIG. 1. Said support facility 10 also has a plurality of tablet compartments which are filled with the required medicaments in the automatic tablet dispenser 50, are checked for completeness and correctness at a subsequent control station 60, and finally the content of the support facility is transferred into the tablet container at a decanting station. In a presently preferred embodiment of the invention, the support facility 10 is designed such that it can directly pick up a tablet container 1 and convey it through the entire tablet filling system. In the illustrated exemplary embodiment, the tablet container 1 is designed as a blister pack. In the subsequent specification, the tablet containers 1 are thus also referred to as blisters and the support facility 10 is referred to as a pseudo-blister. Each blister comprises 4×7 tablet compartments 2, i.e., tablet compartments for four intake times on each day of the week. Each blister 1 is insertable into a pseudo-blister 10 and can be locked in a fixed position by shutting a lid of the pseudo-blister comprising 28 openings corresponding to the tablet compartments 2.

Each pseudo-blister 10 is provided with a transponder as an information carrier 11, which transponder is writable and readable in a contactless manner. The allocation means 40 write the prescription data REZ and the patient identification PAT-ID onto the information carrier 11 so that this information can be queried at any time throughout the entire journey of the pseudo-blister 10 through the tablet filling system. The prescription data REZ constitute the control element during the process. To allow easier control by an operator, the information carrier 11 could also contain a printable field in which the prescription data and the patient identification are printed in readable form or in a coding comprehensible to the operator. It should be mentioned that the data specific to the patient order (medicament, number etc.) can be subjected to a plausibility check regarding mutual compatibility, overdosage, contraindications, with such a plausibility check suitably already being integral with the reception means 30.

Transponder readers which read out the content of the information carrier 11 and, based on the reading result, ensure proper material flow are located at each point in the tablet filling system according to the invention where some kind of decision must be made (=decision stations). If actions are to be performed at any station, defective results which might possibly occur (error identifications) are finally written onto the information carrier 11. Results from all decision stations are transmitted additively to a superordinate control computer and are stored for the long term. Pseudo-blisters in which errors have occurred, which, for example, have been filled incorrectly at the stations, are removed from the material flow and their content is discarded. Subsequently, this order is restarted.

The automatic tablet dispenser 50 is assembled in a modular fashion from a plurality of individual tablet dispensing stations 51 so that an independent tablet dispensing station 51 can be used for each product class of medicaments. The tablet dispensing stations 51 have the function of transferring pills from a storage container into the correct tablet compartments 2 of a tablet container 1.

Figure 2:
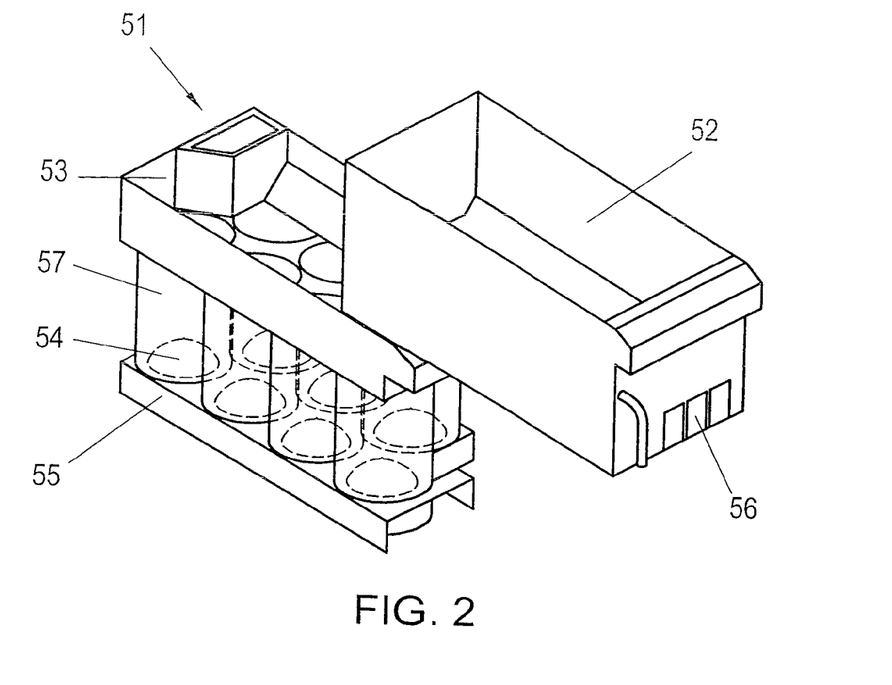
FIG. 2 shows a tablet dispensing station in perspective view.
Figure 3:
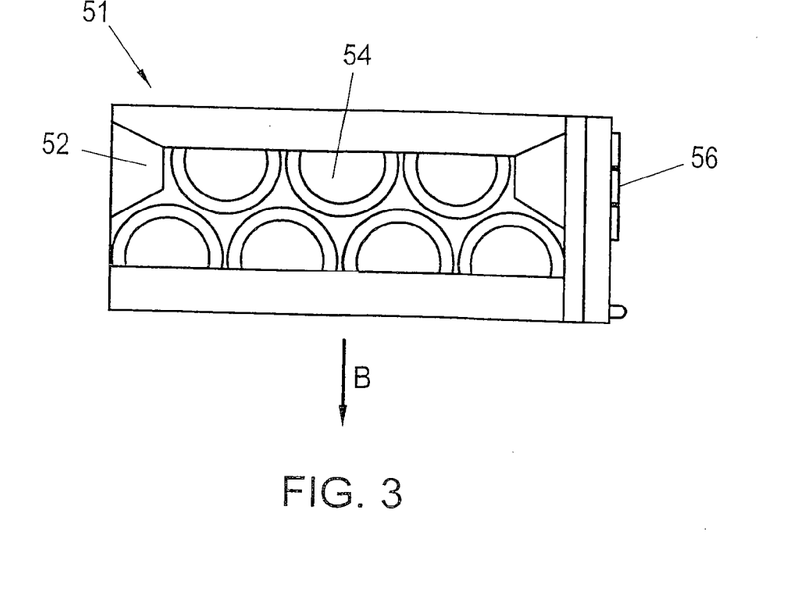
FIG. 3 shows a top view of the tablet dispensing station of FIG. 2.
Figure 4:
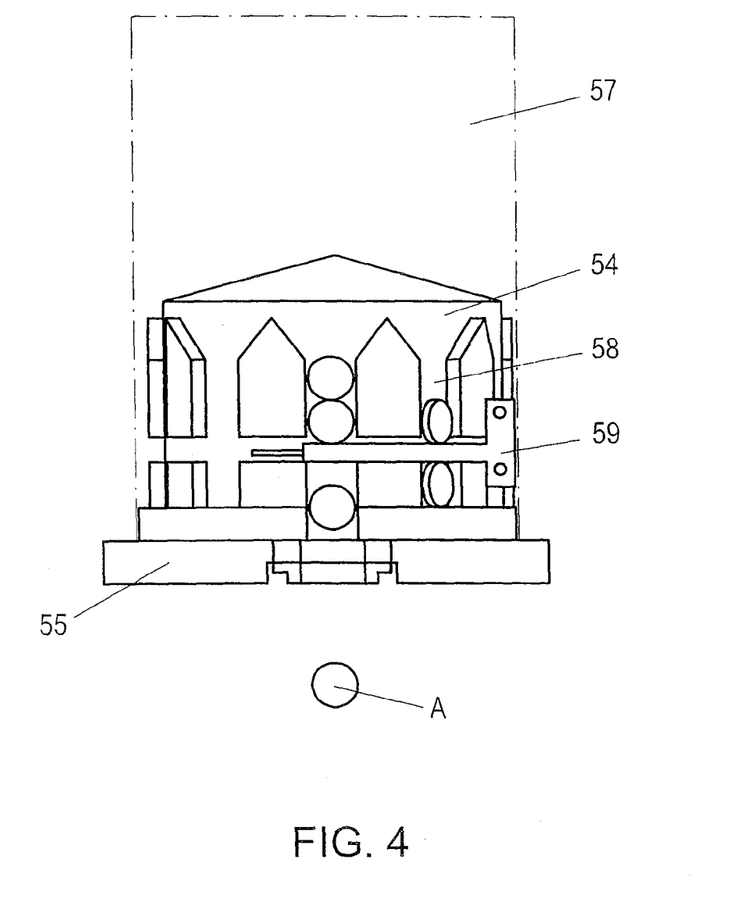
FIG. 4 shows a side view of a rotary tablet dispensing unit used in the tablet dispensing station.

An embodiment according to the invention of a tablet dispensing station 51 is illustrated in FIGS. 2 and 3 in perspective and top views, respectively. The tablet dispensing station 51 comprises a plurality of tablet dispensing units 54, seven in the present case, which correspond to the seven rows of weekday-tablet compartments. Arrow B in FIG. 3 indicates the transport direction of the tablet containers and of the pseudo-blisters, respectively, beneath the tablet dispensing station 51. The pseudo-blister is clocked through the automatic dispenser in such a way that medicaments for seven weekdays at a time can be dispensed in parallel. One can seen that, in order to achieve the compact design necessary for this purpose, the tablet dispensing units 54 are arranged in two rows which are offset against each other. Each tablet dispensing unit 54 is designed as a rotary dispensing unit and comprises a cylindrical pipe 57 for supplying the tablets from a tablet magazine 53 common to all tablet dispensing units of a tablet dispensing station 51. The tablet magazine 53 is in turn connectable to a replaceable buffer container 52 containing an excess supply of tablets. Colour codings 56 are provided both on the tablet magazine 53 and on the buffer container 52 in order to provide a simple possibility for an operator to check as to whether, as a matter of fact, the correct buffer containers are being used. Hardware-related codings can likewise be provided by means of which it is prevented that non-associated buffer containers can be inserted into the tablet magazine, as will be explained hereinbelow in further detail. The tablet dispensing unit 54 can be designed as a rotary dispensing unit according to U.S. Pat. No. 5,803,309, the disclosure of which is herewith incorporated by reference. FIG. 4 shows a side view of the rotary dispensing unit 54 according to U.S. Pat. No. 5,803,309. The actual rotary unit comprising compartments 58 for stacking tablets A in column form on top of each other in the compartments can be seen below the tablet feeding cylinder 57. A distance piece 59 serves for dispensing only individual tablets A via an ejection unit 55 downwards, where they drop directly into a tablet compartment of the tablet container or of the pseudo-blister, respectively.

The control of the filling process in the automatic tablet dispenser 50 is effected as follows. On the information carrier 11 of the pseudo-blister 10, which information carrier is designed as a transponder, it is stored and detectable, respectively, in the form of prescription data REZ how much must be taken from which tablet dispensing station 51. Clock positioning ensures that the respective number of pieces of a medicament is dispensed to the proper "time-of-day tablet compartment". A pseudo-blister is served for one medicament exclusively by one tablet dispensing station 51. In addition to the information carrier, the pseudo blister is hard-coded. Thus, the positioning of the pseudo-blister can be checked via light scanners. While the pseudo-blister is clocked forward, the next dispensing process is being prepared in the tablet dispensing station 51. For this purpose, it is checked in the respective rotor 54 by means of a light barrier as to whether a medicament is present in the subsequent compartment 58 of the rotor. If the medicament is absent in said rotor compartment 58, the process of positioning the rotor is continued until a compartment filled with a medicament is located right in front of the ejection unit 55. The dispensing process is monitored via a fork light barrier (not illustrated). A signal edge analysis of said fork light barrier ensures that the correct number of medicaments has been dispensed.

Each dispensing process is monitored and checked by the hardware of the automatic tablet dispenser. Errors are written directly into the transponder and, in addition, are communicated to a superordinate control computer. Control means 60 identifying and eliminating pseudo-blisters 11 which have been filled incorrectly or are otherwise defective are located downstream of each automatic tablet dispenser. The content of those eliminated pseudo-blisters is subsequently recycled, and the pseudo-blister is transported back to the system's starting point. Orders the contents of which have been commissioned incorrectly are started once again.

Master data (number of the automatic tablet dispenser, product name of the medicaments to be dispensed, software version, hardware version etc.) are written into the hardware of an automatic tablet dispenser after calibration (allocation of the medicament to be dispensed to the dispensing stations).

The fill level of the buffer containers 52 is controlled by a light barrier. If a buffer container 52 is empty, it must be replaced. The tablet magazine 53 is provided so that the affected tablet dispensing station 51 can carry on operating nonetheless. The filling volume of the tablet magazine 53 should thereby be chosen such that refilling of the buffer container is possible without interrupting the dispensing process. In order to prevent products from being mixed up, each buffer is, on the one hand, colour-coded and, on the other hand, hard-coded. The hardware of a tablet dispensing station 51 is informed through an interaction that its buffer container 52 is in the process of being replaced. The person performing the refilling process can determine based on the colour coding as to whether the correct buffer container has been attached or inserted, respectively. The hardware detects that a new buffer container has been attached or inserted, respectively. Each buffer container is provided with an electronic data carrier onto which the product information was written during the filling of the buffer container. Said information is then read out by the hardware of the tablet dispensing station. If the data of the buffer container correspond to the master data of the hardware of the tablet dispensing station, the buffer container is unlocked. Thereupon, the mechanical lock separating the buffer container 52 from the tablet dispensing magazine 53 can be removed. Subsequently, the medicaments drop into the tablet dispensing magazine 53. Each refilling process is co-logged and reported to the higher-ranking control system.

The higher-ranking control system is in charge of "tracking and tracing". The history of each automatic tablet dispenser of the tablet filling system is filed in a database. Thus, it is possible to reconstruct at any time which patient order was provided with which medicaments (charge) at what time.

Empty buffer containers are filled with medicaments at a particular workstation. In doing so, one must be careful to make sure that the correct medicaments are placed in the buffer containers intended therefor.

The abrasion from the medicaments causes the tablet dispensing station to be soiled after a finite number of tablets have been dispensed. Depending on the degree of soiling, the quality of the dispensing process will decrease. Therefore, cleaning intervals at which the tablet dispensing stations are cleaned in a kind of "washing plant" are defined.

After the individual patient orders have been processed, the contents of the filled pseudo-blisters are checked for correctness and completeness by the control means 60, using imaging systems. The results are transferred to a higher-ranking control system and stored along with the client data. In case of a negative result, the pseudo-blister is removed from the material flow and is either inspected manually or recycled, whereby the order is started once again.

Downstream of the control means 60, properly filled and faultless tablet containers are separated from their support facilities, sealed by closing means 70 and imprinted with patient-specific data at a printing station 80.

Finally, completely sealed and imprinted tablet containers are collected by collecting means 90 and optionally sorted. For this purpose, each tablet container must exhibit machine-readable patient identifications, e.g., a bar-code.

The higher-ranking control system receives the orders to be processed from a HOST system. In addition, the material flow of the pseudo-blisters is guaranteed and checked. Each result of the individual pseudo-blisters is recorded in a database. The results of the control station are also recorded in this database. A control panel provides information about the condition of the overall system. The operators of the tablet filling system have to log into the system in order to be allowed to perform activities (refilling process, product replacement, maintenance etc.).

The invention claimed is:

1. A method for automatically filling tablets into tablet containers comprising at least one tablet compartment for receiving tablets, the method comprising:
   receiving a patient order containing a patient identification and at least one prescription comprising prescription data regarding the types of tablets to be taken by the patient and instructions for taking said tablets;
   allocating the prescription data and patient identification to respective tablet containers by transmitting the prescription data and patient identification to one of several information carriers and the allocation of a respective information carrier to one tablet container at a time;
   automatically filling at least one tablet compartment of a respective tablet container by means of at least one automatic tablet dispenser containing supplies of a plurality of tablet types,
   wherein the number of tablets of the respective types of tablets to be taken by a patient at certain times is determined from the prescription data and a tablet compartment of a tablet container is allocated to each determined time for taking the tablets and the tablets thus determined are filled in the tablet container for each determined time for taking them into the respective tablet compartment that has been allocated,
   wherein if errors occur during the implementation of the tablet filling process for the tablet container, an error identification is written onto the information carrier of the tablet container and the tablet filling process is stopped and the tablet container is eliminated centrally at the end of the filling process, wherefore prior to each processing step each tablet container is checked as to whether the information carrier contains an error identification and, upon detection of such an error identification, the respective processing step is not carried out; and
   sealing and delivering the filled tablet containers, wherein upon receiving the patient order, a plausibility check of the prescription data regarding a possible overdosage and the mutual compatibility between tablet types is carried out and, in case an overdosage or an incompatibility is detected, the patient order is rejected.

2. A tablet filling method according to claim 1, wherein the allocation of prescription data and patient identification to respective tablet containers comprises the transmission of prescription data and patient identification to one or several information carriers and the allocation of a respective information carrier to one tablet container at a time.

3. A tablet filling method according to claim 2, wherein an electronic data carrier, which preferably is writable and readable in a non-contact manner, or a printable substrate such as a bar-code label is provided as an information carrier.

4. A tablet filling method according to claim 3, wherein if errors occur during the implementation of the tablet filling process for a tablet container, the tablet filling process is stopped and the tablet container is eliminated.

5. A tablet filling method according to claim 4, wherein if errors occur during the implementation of the tablet filling process for a tablet container, error identifications are written onto the information carrier allocated to said tablet container and tablet containers marked with error identifications in this way are eliminated during the delivery.

6. A tablet filling method according to claim 5, wherein prior to each processing step of the tablet filling process, it is checked for each tablet container as to whether the information carrier allocated to said tablet container contains an error identification and, upon detection of such an error identification, the respective processing step is not carried out.

7. A tablet filling method according to claim 2, wherein the automatic filling of at least one tablet compartment of a respective tablet container by at least one automatic tablet dispenser comprises conveying the tablet containers and the information carriers allocated thereto jointly through the at least one automatic tablet dispenser;
   reading out the prescription data stored on the information carrier by the respective automatic tablet dispenser;

checking by means of the respective automatic tablet dispenser as to whether the supplies of tablet types stored in it correspond to one of the tablet types contained in the prescription data and, in case of correspondence, determining the number of tablets of the respective types of tablets to be taken by the patient at certain times and allocating a tablet compartment to each determined time for taking the tablets, and filling the determined tablets into the respective tablet compartment that has been allocated.

8. A tablet filling method according to claim 2, wherein if errors occur during the implementation of the tablet filling process for a tablet container, error identifications are written onto the information carrier allocated to said tablet container and tablet containers marked with error identifications in this way are eliminated during the delivery.

9. A tablet filling method according to claim 8, wherein prior to each processing step of the tablet filling process, it is checked for each tablet container as to whether the information carrier allocated to said tablet container contains an error identification and, upon detection of such an error identification, the respective processing step is not carried out.

10. A tablet filling method according to claim 1, wherein the tablet containers are provided with at least one of information derived from the prescription data, instructions for taking the tablets, and the patient identification, by at least one of imprinting and labeling the tablet container.

11. A tablet filling method according to claim 1, wherein the delivery of the filled tablet containers comprises collecting all tablet containers belonging to a respective patient order.

12. A system for automatically filling tablets into tablet containers comprising at least one tablet compartment for receiving tablets, the system comprising:

reception means for receiving a patient order containing a patient identification and at least one prescription comprising prescription data regarding the types of tablets to be taken by the patient and instructions for taking said tablets;

allocation means for allocating the prescription data and patient identification to respective tablet containers, which allocation means are designed for transmitting the prescription data and patient identification to one or several information carriers and for allocating a respective information carrier to one tablet container at a time;

at least one automatic tablet dispenser containing supplies of a plurality of tablet types for automatically filling at least one tablet compartment of a respective tablet container, wherein the allocation means or the automatic tablet dispenser is/are designed for determining, from the prescription data, the number of tablets of the respective types of tablets to be taken by a patient at certain times and for allocating a tablet compartment of a tablet container to each determined time for taking the tablets, and the automatic tablet dispenser is designed for filling the tablet container with the tablets thus determined for each determined time for taking them into the tablet compartment of the respective tablet container, which compartment has been allocated, wherein if errors occur during the implementation of the tablet filling process for the respective tablet container, the tablet filling process is stopped and the respective tablet container is eliminated, wherein the information carriers are designed for receiving error identifications, and control means are provided which are designed for reading the error identifications from the information carriers and eliminating tablet containers marked with error identifications at the end of the filling process; and decision stations that ensure proper material flow at each point in the tablet filling system based on the read out content of the information carrier; and closing means for sealing the filled tablet containers, wherein the reception means are designed for checking the prescription data for a possible overdosage and the mutual compatibility between tablet types and for rejecting the patient order in case an overdosage or an incompatibility is detected.

13. A tablet filling system according to claim 12, wherein the allocation means are designed for transmitting the prescription data and patient identification to one or several information carriers and for allocating a respective information carrier to one tablet container at a time.

14. A tablet filling system according to claim 13, wherein the information carrier is an electronic data carrier, which is writable and readable in at least one of a non-contact manner, and a printable substrate such as a bar-code label.

15. A tablet filling system according to claim 14, wherein for each tablet container a support facility is provided on which the tablet container is conveyable through the tablet filling system.

16. A tablet filling system according to claim 15, wherein the information carrier is placed on the support facility.

17. A tablet filling system according to claim 13, wherein the automatic tablet dispenser is designed for reading out the prescription data stored on the information carrier and for filling tablets into tablet compartments of the tablet container allocated to the information carrier according to the number of tablets of the respective types of tablets to be taken by the patient at certain times, which number is determinable from the prescription data.

18. A tablet filling system according to claim 13, wherein the information carriers are designed for receiving error identifications, and control means are provided which are designed for reading the error identifications from the information carriers and eliminating tablet containers marked with error identifications.

19. A tablet filling system according to claim 13, wherein for each tablet container a support facility is provided on which the tablet container is conveyable through the tablet filling system.

20. A tablet filling system according to claim 12, wherein for each tablet container a support facility is provided on which the tablet container is conveyable through the tablet filling system.

21. A tablet filling system according to claim 12, wherein the information carrier is placed on the support facility.

22. A tablet filling system according to claim 12, wherein each automatic tablet dispenser comprises a plurality of tablet dispensing stations, each containing a supply of a tablet type and being designed for dispensing an adjustable number of tablets to random tablet compartments of the tablet containers.

23. A tablet filling system according to claim 12, wherein at least one of printing and labeling means for providing the tablet containers with information derived from at least one of the prescription data, instructions for taking the tablets, and the patient identification.

24. A tablet filling system according to claim 12, wherein collecting means are provided for collecting all tablet containers belonging to a respective patient order.

25. A tablet filling system according to claim 12, wherein each tablet dispensing station comprises a plurality of tablet dispensing units supplied by a common tablet magazine, with the tablet dispensing units preferably being designed as rotary dispensing units.

26. A tablet filling system according to claim 25, wherein the tablet magazine is connectable to a replaceable buffer container.

* * * * *